US 7,642,258 B2

(12) United States Patent
Chang et al.

(10) Patent No.: US 7,642,258 B2
(45) Date of Patent: *Jan. 5, 2010

(54) COMBINATION OF BRIMONIDINE AND TIMOLOL FOR TOPICAL OPHTHALMIC USE

(75) Inventors: Chin-Ming Chang, Tustin, CA (US); Gary J. Beck, Fullerton, CA (US); Cynthia C. Pratt, Mission Viejo, CA (US); Amy L. Batoosingh, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 227 days.

This patent is subject to a terminal disclaimer.

(21) Appl. No.: 11/844,476

(22) Filed: Aug. 24, 2007

(65) Prior Publication Data

US 2008/0103153 A1  May 1, 2008

Related U.S. Application Data

(63) Continuation-in-part of application No. 10/685,941, filed on Oct. 14, 2003, now Pat. No. 7,320,976, which is a continuation of application No. 10/126,790, filed on Apr. 19, 2002, now Pat. No. 7,030,149.

(51) Int. Cl.
*A61K 31/498* (2006.01)
*A61K 31/5377* (2006.01)
*A61K 31/141* (2006.01)

(52) U.S. Cl. .................... 514/249; 514/235.8; 514/393; 514/397; 514/398

(58) Field of Classification Search .................. None
See application file for complete search history.

(56) References Cited

U.S. PATENT DOCUMENTS

| | | | |
|---|---|---|---|
| 3,890,319 | A | 6/1975 | Danielewicz et al. |
| 4,195,085 | A | 3/1980 | Stone |
| 4,861,760 | A | 8/1989 | Mazuel et al. |
| 5,021,410 | A | 6/1991 | Burke |
| 5,502,052 | A | 3/1996 | DeSantis |
| 5,856,329 | A | 1/1999 | Wheeler et al. |
| 6,159,458 | A | 12/2000 | Bowman et al. |
| 6,174,524 | B1 | 1/2001 | Bawa et al. |
| 6,194,415 | B1 | 2/2001 | Wheeler et al. |
| 6,248,741 | B1 | 6/2001 | Wheeler et al. |
| 6,294,563 | B1 | 9/2001 | Garst |
| 6,316,441 | B1 | 11/2001 | Dean et al. |
| 6,410,045 | B1 | 6/2002 | Schultz et al. |
| 6,440,964 | B1 | 8/2002 | Cagle et al. |
| 6,441,047 | B2 | 8/2002 | Desantes, Jr. |
| 6,562,873 | B2 | 5/2003 | Olejnik et al. |
| 6,627,210 | B2 | 9/2003 | Olejnik et al. |
| 6,740,664 | B2 | 5/2004 | Cagle et al. |

2002/0128267 A1   9/2002  Bandyopadhyay et al.

OTHER PUBLICATIONS

Arici, et al., "A Short Term Study of the Additive Effect of Timolol and Brimonidine on Intraocular Pressure," www.nature.com/eye/journal/v16/n1/full/6700035a, Eye, 2002, vol. 16, No. 1, pp. 39-43.
Bhatt, et al., "Prospective Survey of Adverse Reactions to Topical Antiglaucoma Medications in a Hospital Population," Eye Advance Online Publication, Aug. 6, 2004, Clinical Study.
Craven et al, "Efficacy and Safety of the IOP-Lowering Fixed Combination Brimonidine 0.2%/Timolol 0.5%," M200510403E.1.doc, one page.
Goni et al, "Comparison of Fixed-Combination Brimonidine and Timolol With Concomitant Use of the Individual Components in Glaucoma and Ocular Hypertension: Achievement of Clinically Relevant IOP Reductions," 5th International Glaucoma SYmposium (IGS)Mar. 2005, Cpae Town, South Africa, Funding by Allergan.
Goni, "12-week study comparing the fixed combination of brimonidine and timolol with concomitant use of the individual components in patients with glaucoma and ocular hypertension," European Journal of Ophthalmology, vol. 15, No. 5, 2005, pp. 581-590.
Hommer, A.B., et al., "Efficacy and Safety of Unoprostone, Dorzolamide, and Brimonidine in Adjunctive Therapy to Timolol in Pateitnts with primary open-angle glaucoma and ocular hypertension," Investigative Ophthalmology & Visual Science,Abstract XP009014430, (vol. 42, No. 4, Supp. Mar. 15, 2001, p. 554) (XP009014419).
Hoyng, P.F., et al., "Pharmacological Therapy of glaucoma," Drugs, vol. 59, No. 3, Mar. 2000 pp. 411-434.
Jackson, et al., "Cardiovascular Effects of Timolol, Brimonidine and Brimonidine/Timolol in Combination," IOVS, 2001, vol. 42, No. 4, p. S418.
Larsson, "Aqueous Humor Flow in Normal Human Eyes Treated With Brimonidine and Timolol, Alone and In Combination," Abstract, AN99050646.
Larsson, L.I., "Aqueous humor flow in normal human eyes treated with brimonidine and timolol, alone and in combination," Arch Ophthalmol, vol. 119, Apr. 2001, p. 492-495 (XP009014425).
Sall, et al., "A Comparison of the Ocular Hypotensive Effect of Dorzolamide Hydrochloride," Abstract, IOVS, 2001, vol. 42, No. 4, p. S822.
Schuman, J.S., "Clinical experience with brimonidine 0.2% and timolol 0.5% in glaucoma and ocular hypertentsion," Survey of Ophthalmology, Vo. 41, Supp. 1, 1996, p. S27-S37 (XP009014391).
Serle, JB, A Comparison of the Safety and Efficacy of Twice Daily Brimonidine 0.2%Versus Betaxolol 0.25% in Subjects With Elevated Intraocular PRessure. The Brimonidine Study Group III. Survey Opthalmology, 1996, vol. 41 (Suppl.1), Abstract.
Simmons, Steven, et al., "Three-Month Comparison of Brimonidine and Latanoprost as Adjunctive Therapy in Glaucoma and Ocular Hypertension Patients Uncontrolled on β-blockers," Ophthalmologyh, vol. 109, No. 2, 2002, pp. 307-314.
Stewart, W.C., "Perspectives in the medical treatment of glaucoma," Current Opinion in Ophthalmology, vol. 10, No. 2, Apr. 1999, pp. 99-109.

(Continued)

*Primary Examiner*—Brian-Yong S Kwon
(74) *Attorney, Agent, or Firm*—Allergan, Inc.; John E. Wurst

(57) ABSTRACT

Disclosed are pharmaceutical compositions comprising brimondine and timolol for topical ophthalmic delivery and a method of treatment comprising administering said composition when indicated for glaucoma and associated conditions such as elevated intraocular pressure in the eyes of humans.

9 Claims, No Drawings

OTHER PUBLICATIONS

Stewart, et al., "Cardiovascular Effects of Timolol Maleate, Brimonidine or Brimonidine/Timolol Maleate in Concomitant Therapy," Acta Ophtyalmologica Scandinavica, 2002, 80(3), pp. 277-281.

Wang, R.F., et al., "Comparison of the ocular hypotensive effect of brimonidine, dorzolamide, latanoprost, or artificial tears added to timolol in glaucomatous monkey eyes," J. of Glaucoma 9:458-62.

Yuksel, N., et al., "The short-term effect of adding brimonidine 0.2% to timolol treatment in patients with open-angle glaucoma," Ophthalmologica, vol. 213 (1999), pp. 228-233.

Drug Information Brochure on Alphagan, Allergan, 2001.

Drug Information Brochure on Timoptic, Merck Sharp Dohme-Cibret MSD, Apr. 2001.

"Brimonidine," Patient Information Brochure, www.ausdi.com, 2000, pp. 1-6.

Airaksinen et al.; "A Double Masked Study of Timolol and Pilocarpine Combined"; American Journal of Ophthalmology, vol. 104; Dec. 15, 1987.

Clineschmidt et al.; "A Randomized Trial in Patients Inadequately Controlled with Timolol Alone Comparing the Dorzolamide-Timolol Combination to Monotherapy with Timolol or Dorzolamide"; American Journal of Ophthalmology, vol. 105; Oct. 1998.

Merck & Co., Inc. "Cosopt® (dorzolamide hydrochloride-timolol maleate ophthalmic solution) data sheet"; NDA 20-869/S-034; 1998.

Diestelhorst et al; "Comparison of Two Fixed Combinations of Latanoprost and Timolol in Open-Angle Glaucoma"; Graege's Arch Clin Exp Ophthalmol; 236:577-581; 1998.

Larsson; "Aqueous Humor Flow in Normal Human Eyes Treated with Brimonidine and Timolol, Alone and in Combination"; Arch Ophthalmol, vol. 119; Apr. 2001.

Leblanc; "Twelve-Month Results of an Ongoing Randomized Trail Comparing Brimonidone Tartrate 0.2 % and Timolol 0.5 % Given Twice Daily in Patient With Glaucoma or Ocular Hypertension"; American Journal of Ophthalmology, vol. 105; Oct. 1998; pp. 1961-1967.

MaClure, et al; "Effect on the 24-Hour Diurnal Curve of Intraocular Pressure on a Fixed Ration Combination of Timolol 0.5% and Pilocarpine 2% in Patients With COAG Not Controlled on Timolol 0.5%"; British Journal of Ophthalmology; 1989; pp. 827-831.

Merck & Co., Inc. "Trusopt® (Dorzolamide Hydrochloride Ophthalmic Solution) data sheet"; NDA 20-408/S-033; Jul. 1997.

Strohmaier, et al.; "The Effecacy and Safety of the Dorzolamide-Timolol Combination Versus the Concomitant Administration of its Components"; American Journal of Ophthalmology, vol. 105; Oct. 1998; pp. 1936-191944.

Hecht; "Ophthalmic Preparations" Remington: The Science and Practice of Pharmacy, $20^{th}$ edition; 1995; pp. 819-835.

Merck & Co., Inc. "Timoptic® (0.25% and 0.5% Timolol Malate Ophthalmic Solution"; NDA 18-086/S-070, NDA 18-086/S-072; 1995.

Hi Tech Pharmacal; "Letter regarding abbreviated new drug application"; Apr. 22, 2009.

COMBINATION OF BRIMONIDINE AND TIMOLOL FOR TOPICAL OPHTHALMIC USE

CROSS REFERENCE TO RELATED APPLICATIONS

The present application is a continuation-in-part application of pending prior application Ser. No. 10/685,941, filed on Oct. 14, 2003 now U.S. Pat. No. 7,320,976 for COMBINATION OF BRIMONIDINE AND TIMOLOL FOR TOPICAL OPHTHALMIC USE, which is continuation application of application Ser. No. 10/126,790, filed on Apr. 19, 2002 now U.S. Pat. No. 7,030,149 for COMBINATION OF BRIMONIDINE AND TIMOLOL FOR TOPICAL OPHTHALMIC USE.

BACKGROUND OF THE INVENTION

This invention relates to the topical ophthalmic use of brimonidine in combination with timolol when indicated for treatment of glaucoma or ocular hypertension. Such combinations or formulations are available for separate use in the ophthalmic art and have been combined in serial application during the course of treatment of glaucoma. However, there are concerns and expressed reservations in the ophthalmic community about patient compliance when the patient is required to administer separate medications to treat a single disease or condition such as glaucoma. There is, moreover, a long felt need for an effective and safe topical ophthalmic pharmaceutical composition including brimonidine and timolol which has increased stability and requires a lower effective concentration of preservative as compared to the individual agents taken alone. Finally, there is a need to increase the efficacy of many topical ophthalmic agents, without increasing the systemic concentration of such topical agents, since it is well known that many of such topically-applied ophthalmic agents cause systemic side effects, e.g. drowsiness, heart effects, etc. Unexpectedly it has been discovered that brimonidine in combination with timolol meets these criteria.

Brimonidine is disclosed in U.S. Pat. No. 3,890,319. The use of brimonidine for providing neuroprotection to the eye is disclosed in U.S. Pat. Nos. 5,856,329; 6,194,415 and 6,248,741.

Timolol, as an ophthalmic drug, is disclosed in U.S. Pat. Nos. 4,195,085 and 4,861,760.

DESCRIPTION OF THE INVENTION

Brimonidine is an alpha adrenergic agonist represented by the following formula:

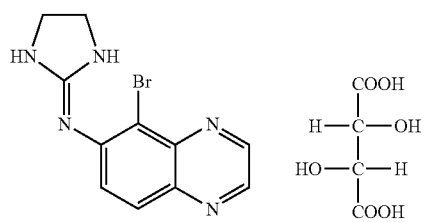

The chemical name for brimonidine is 5-Bromo-6-(2-imidazolidinylideneamino)quinoxaline L-tartrate.

Brimonidine free base is the neutral form of brimonidine, i.e. 5-Bromo-6-(2-imidazolidinylideneamino)quinoxaline:

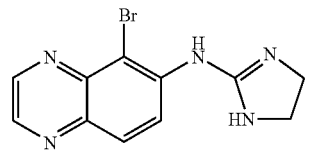

Timolol is a beta adrenergic agent represented by the following formula:

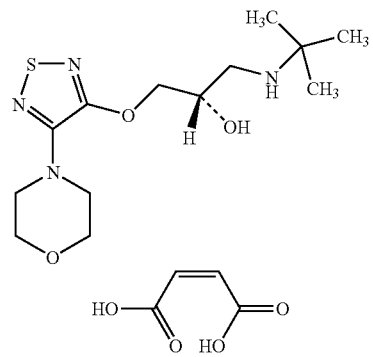

Timolol free base is the neutral form of timolol:

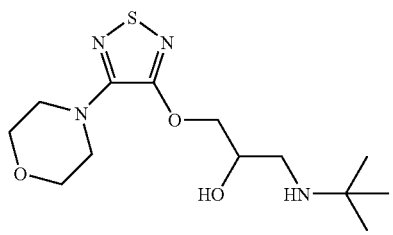

Brimonidine is available from Allergan, Inc., Irvine, Calif. as an ophthalmic pharmaceutical product having the name Alphagan®.

Timolol is available from various sources, including Merck Co., Rahway, N.J.

The compositions of the present invention are administered topically. The dosage is 0.001 to 1.0, e.g. mg/per eye BID; wherein the cited mass figures represent the sum of the two components, brimonidine and timolol. The compositions of the present invention can be administered as solutions in a suitable ophthalmic vehicle.

In forming compositions for topical administration, the mixtures are preferably formulated as 0.01 to 0.5 percent by weight brimonidine and 0.1 to 1.0 percent by weight timolol solution in water at a pH of 4.5 to 8.0, e.g. about 6.9. While the precise regimen is left to the discretion of the clinician, it is recommended that the solution be topically applied by placing one drop in each eye two times a day. Other ingredients which may be desirable to use in the ophthalmic preparations of the present invention include preservatives, co-solvents and viscosity building agents.

Antimicrobial Preservative:

Ophthalmic products are typically packaged in multidose form. Preservatives are thus required to prevent microbial contamination during use. Suitable preservatives include:

benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, typically such preservatives are employed at a level of from 0.004% to 0.02%. In the compositions of the present application the preservative, preferably benzalkonium chloride, may be employed at a level of from 0.001% to less than 0.01%, e.g. from 0.001% to 0.008%, preferably about 0.005% by weight. It has been found that a concentration of benzalkonium chloride of 0.005% is sufficient to preserve the compositions of the present invention from microbial attack. This concentration may be advantageously compared to the requirement of 0.01% benzalkonium chloride to preserve timolol in the individual, commercially-available ophthalmic products. Moreover, it has been found that adequate lowering of intraocular pressure has been obtained when administering the compositions of this invention twice a day as compared to the FDA-approved regimen wherein brimonidine ophthalmic solution, i.e. Alphagan® ophthalmic solution is administered three times a day and timolol ophthalmic solution, i.e. Timoptic® ophthalmic solution is administered twice a day. This results in the exposure of the patient to 67% and 50% of benzalkonium chloride, with the compositions of this invention, as compared to the administration of Alphagan® and Timoptic®, respectively. In FDA-approved adjunctive therapy, wherein Alphagan® and Timoptic® are serially administered, the patient is exposed to almost three times the concentration of benzalkonium chloride as compared to the administration of the compositions of this invention twice a day. (It is noted that it is known that benzalkonium chloride at high concentrations is cytotoxic. Therefore, minimizing the patient's exposure to benzalkonium chloride, while providing the preservative effects afforded by benzalkonium chloride, is clearly desirable.)

Co-Solvents:

The solubility of the components of the present compositions may be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Typically such co-solvents are employed at a level of from 0.01% to 2% by weight.

Viscosity Agents:

Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Such viscosity building agents include as examples polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art. Such agents are typically employed at a level of from 0.01% to 2% by weight.

Compositions having a combination of timolol free base and brimonidine tartrate are more stable than the combination of timolol maleate and brimonidine tartrate. Compositions having a combination of timolol free base and brimonidine free base may have additional stability.

The present invention further comprises an article of manufacture comprising packaging material and a pharmaceutical agent contained within said packaging material, wherein the pharmaceutical agent is therapeutically effective for lowering intraocular pressure and wherein the packaging material comprises a label which indicates the pharmaceutical agent can be used for lowering intraocular pressure and wherein said pharmaceutical agent comprises an effective amount of brimonidine and an effective amount of timolol.

The following example is a representative pharmaceutical composition of the invention for topical use when indicated for treating glaucoma.

EXAMPLE I

The combination of active pharmaceutical ingredients is as follows:

Brimonidine Tartrate 0.20% (w/v) and Timolol Maleate 0.68% (w/v)

(Equivalent to 0.50% (w/v) timolol)

The Brimonidine-Timolol combination formulation presented in the Table, below, is a sterile, preserved, aqueous solution. The formulation vehicle is based upon a timolol ophthalmic solution which contains an isotonic phosphate buffer system at pH 6.9. The formulation preservative is benzalkonium chloride (BAK) at a concentration of 0.005% (w/v) (50 ppm). The formulation passes regulatory required preservative efficacy testing (PET) criteria for USP (United States Pharmacopoeia) and EP (European Pharmacopoeia-A and -B over 24 months.

TABLE

| Ingredient | Function | Concentration, % (w/v) |
|---|---|---|
| Brimonidine Tartrate | Active | 0.2 |
| Timolol Maleate, EP | Active | 0.68[1] |
| Benzalkonium Chloride, NF, EP | Preservative | 0.005 |
| Sodium Phosphate, monobasic monohydrate, USP | Buffer | 0.43 |
| Sodium Phosphate, dibasic heptahydrate, USP | Buffer | 2.15 |
| Sodium Hydroxide, NF | pH adjust | Adjust pH to 6.9 |
| Hydrochloric Acid, NF | pH adjust | Adjust pH to 6.9 |
| Purified Water, USP, EP | Solvent | q.s. ad |

[1]Equivalent to 0.5% (w/v) Timolol, free base

The pharmaceutical composition of Example I is used in the clinical study reported below.

EXAMPLE II

Objectives

To compare the safety and efficacy of twice-daily dosed brimonidine tartrate 0.2%/timolol 0.5% ophthalmic solution combination (henceforth referred to as Combination) with that of twice-daily dosed timolol ophthalmic solution 0.5% (henceforth referred to as Timolol) and three-times-daily dosed ALPHAGAN® (brimonidine tartrate ophthalmic solution) 0.2% (henceforth referred to as Brimonidine) administered for three months (plus 9-month masked extension) in patients with glaucoma or ocular hypertension.

Methodology:

Structure: multicenter, double-masked, randomized, parallel-group, active control Randomization: patients were randomized to one of the 3 masked treatment groups (Combination, Brimonidine or Timolol) based on an even allocation at each site Visit Schedule: prestudy, baseline (day 0), week 2, week 6, month 3, month 6, month 9, and month 12

Number of Patients (Planned and Analyzed):

560 planned to enroll; 586 enrolled (Combination=193, Brimonidine=196, Timolol=197); 502 completed. Mean (range) age: 62.4 (23 to 87) years; 46.1% (270/586) males, 53.9% (316/586) females.

Diagnosis and Main Criteria for Inclusion:

Diagnosis: ocular hypertension, chronic open-angle glaucoma, chronic angle-closure glaucoma with patent iridotomy, pseudoexfoliative glaucoma or pigmentary glaucoma and requiring bilateral treatment.

Key Inclusion Criteria: ≧18 years, day 0 (post-washout) intraocular pressure (IOP) ≧22 mm Hg and ≦34 mm Hg in each eye and asymmetry of IOP ≦5 mm Hg, best-corrected Early Treatment of Diabetic Retinopathy Study (ETDRS) visual acuity equivalent to a Snellen score of 20/100 or better in each eye.

Key Exclusion Criteria: uncontrolled systemic disease, abnormally low or high blood pressure or pulse rate for age or contraindication to beta-adrenoceptor antagonist therapy, anticipated alteration of existing chronic therapy with agents which could have a substantial effect on IOP, contraindication to brimonidine therapy, allergy or sensitivity to any of the study medication ingredients, anticipated wearing of contact lenses during the study, laser surgery, intraocular filtering surgery or any other ocular surgery within the past 3 months, or required chronic use of other ocular medications during the study (intermittent use of artificial tear product was allowed).

Test Product, Dose and Mode of Administration, Batch Number:

Brimonidine tartrate 0.2%/timolol 0.5% combination ophthalmic solution one drop (~35 μL) instilled in each eye BID in the morning and evening; and vehicle of the Combination ophthalmic solution, one drop (~35 μL) instilled in each eye once daily (QD) in the afternoon (for masking purposes).

Duration of Treatment: 3 months (with a 9-month masked extension)

Reference Therapy, Dose and Mode of Administration, Batch Number:

Active control ALPHAGAN® (brimonidine tartrate ophthalmic solution) 0.2%, one drop (~35 μL) instilled in each eye TID in the morning, afternoon, and evening.

Active control timolol ophthalmic solution 0.5%, one drop (~35 μL) instilled in each eye BID in the morning and evening; and vehicle of the Combination ophthalmic solution, one drop (~35 μL) instilled in each eye once daily (QD) in the afternoon (for masking purposes).

Criteria for Evaluation:

Efficacy:

IOP (hours 0, 2, 7, and 9), patient satisfaction questionnaire, patient comfort of study medication questionnaire, pharmacoeconomic evaluation by investigator Safety:

Adverse events (AE), biomicroscopy, visual acuity (VA), visual field, opthalmoscopy, cup/disc ratio, heart rate, blood pressure, hematology, serum chemistry, urinalysis and pregnancy test.

Other:

Quantitation of plasma brimonidine and timolol concentrations (at selected sites), resource utilization (to be reported upon completion of the 1 year study).

Statistical Methods:

All data were summarized with descriptive statistics, frequency tables, and/or data listings. Safety analyses included all patients who received at least 1 dose of study medication. Analyses were performed for the primary efficacy variable IOP using the intent-to-treat (ITT) population with last observation carried forward (LOCF), and the per protocol population with observed cases.

Ordinal categorical variables were analyzed by the Wilcoxon rank-sum test. Nominal categorical variables were analyzed using Fisher's exact or Pearson's chi-square tests. Within-group changes from baseline for categorical variables were analyzed using the Wilcoxon signed-rank test.

Continuous variables (eg, IOP) were analyzed using analysis of variance (ANOVA). Within-group changes from baseline for continuous variables were analyzed using paired t-tests.

A 2-way ANOVA model with factors for treatment and investigator was used for the analysis of IOP. Comparisons were made between the Combination and each of the 2 monotherapies in a pairwise fashion using contrasts from the ANOVA model, with the same error term. A separate ANOVA model was employed at each hour/visit measurement of IOP. Each of the 2 null hypotheses (Combination versus Timolol and Combination versus Brimonidine) was tested at the 0.05 significance level. Point estimates of the mean treatment differences, as well as 2-sided 95% confidence intervals (CI) of the difference, were provided at each timepoint.

Summary—Conclusions:

Efficacy:

At baseline, mean values of diurnal IOP ranged from 22.2 mm Hg to 24.9 mm Hg in the Combination group, 22.5 mm Hg to 25.0 mm Hg in the Brimonidine group, and 22.3 mm Hg to 24.8 mm Hg in the Timolol group. There were no statistically significant differences between treatment groups.

Mean changes from baseline diurnal IOP at week 2, week 6 and month 3 ranged from:

−5.2 to −7.9 mm Hg in the Combination group

−3.5 to −5.7 mm Hg in the Brimonidine group

−4.5 to −6.4 mm Hg in the Timolol group

The mean decreases from baseline diurnal IOP were statistically significant within each treatment group at each follow-up timepoint (p<0.001).

The mean decrease from baseline diurnal IOP was statistically significantly greater with Combination than with Brimonidine at hours 0, 2, and 7 at all follow-up visits (p<0.001). In addition, clinically significant differences of more than 1.5 mm Hg in mean change from baseline IOP favoring Combination over Brimonidine were seen at hours 0, 2, and 7 at all follow-up visits. At hour 9, the decreases from baseline diurnal IOP were greater for the Combination group than the Brimonidine group at all follow-up visits, although the differences were not statistically significant (p≧0.104). The mean decrease from baseline diurnal IOP was statistically significantly greater with Combination than with Timolol at hours 0, 2, 7 and 9 at all follow-up visits (p≦0.041). In addition, clinically significant differences of more than 1.5 mm Hg in mean change from baseline IOP favoring Combination over Timolol were seen at week 2 (hours 0, 2, and 7), week 6 (hours 2 and 7), and month 3 (hours 0 and 2).

Mean values of diurnal IOP at week 2, week 6 and month 3 ranged from:

15.9 to 18.1 mm Hg in the Combination group 17.4 to 21.5 mm Hg in the Brimonidine group 17.5 to 18.9 mm Hg in the Timolol group Mean values of diurnal IOP were statistically significantly less with Combination than with Brimonidine at hours 0, 2, and 7 at all follow-up visits (p<0.001) and at hour 9 at week 6 and month 3 (p≦0.011). The mean values of IOP at hour 9 at week 2 were lower for the Combination group than the Brimonidine group, although the difference was not statistically significant (p=0.205). In addition, clinically significant differences of more than 1.5 mm Hg in mean IOP favoring Combination over Brimonidine were seen at hours 0, 2, and 7 at all follow-up visits and at hour 9 at month 3.

Mean values of diurnal IOP were statistically significantly less with Combination than with Timolol at hour 0 at week 2 and month 3; and at hours 2, 7 and 9 at all follow-up visits (p≦0.050). The mean values of IOP at hour 0, week 6, were lower for the Combination group than the Timolol group, although the difference was not statistically significant (p=0.102). In addition, clinically significant differences of more than 1.5 mm Hg in mean IOP favoring Combination over Timolol were seen at week 2 (hours 0, 2, and 7), week 6 (hours 2, 7, and 9), and month 3 (hours 2 and 9).

At the month 3 or exit visit, a statistically significantly greater "yes" response to the Investigator Pharmacoeconomic Evaluation was recorded for patients receiving Combination (91.1%, 173/190) than for patients receiving Brimonidine (73.4%, 141/192, p<0.001). A "yes" response was recorded for 92.7% (179/193) of patients receiving Timolol. There were no statistically significant differences in the change from baseline in treatment comfort between Combination and each of the monotherapy groups.

Treatment satisfaction was better than baseline for a statistically significantly greater percentage of patients in the Combination group (23.4%, 36/154) than in the Brimonidine group (13.2%, 20/151, p=0.005). A total of 19.9% (30/151) of patients in the Timolol group reported better treatment satisfaction than baseline.

Safety:

Through month 3 of the study, 53.4% (103/193) of patients in the Combination group, 61.7% (121/196) of the Brimonidine group, and 50.8% (100/197) of the Timolol group experienced one or more adverse events, regardless of causality. The incidences of oral dryness, eye pruritus, foreign body sensation and conjunctival folliculosis were statistically significantly lower with the Combination than with Brimonidine (p≦0.034), while burning and stinging were statistically significantly higher with the Combination than with Brimonidine (p≦0.028). There were no statistically significant differences in adverse events between the Combination and Timolol, except for a statistically significantly higher incidence of eye discharge with the Combination (2.6%, 5/193) compared to Timolol (0%, 0/197; p=0.029). The most frequently reported adverse events (>3% in any treatment group) were as follows, tabulated by descending order in the Combination group:

| Preferred Term | Combination N = 193 | Brimonidine N = 196 | Timolol N = 197 |
|---|---|---|---|
| burning sensation in eye | 23 (11.9%) | 11 (5.6%) | 25 (12.7%) |
| conjunctival hyperemia | 16 (8.3%) | 23 (11.7%) | 11 (5.6%) |
| stinging sensation eye | 13 (6.7%) | 4 (2.0%) | 11 (5.6%) |
| infection (body as a whole) | 11 (5.7%) | 6 (3.1%) | 8 (4.1%) |
| visual disturbance | 6 (3.1%) | 11 (5.6%) | 3 (1.5%) |
| epiphora | 5 (2.6%) | 8 (4.1%) | 3 (1.5%) |
| oral dryness | 4 (2.1%) | 19 (9.7%) | 1 (0.5%) |
| eye pruritus | 3 (1.6%) | 13 (6.6%) | 3 (1.5%) |
| allergic conjunctivitis | 3 (1.6%) | 7 (3.6%) | 0 (0.0%) |
| asthenia | 3 (1.6%) | 6 (3.1%) | 1 (0.5%) |
| foreign body sensation | 2 (1.0%) | 10 (5.1%) | 5 (2.5%) |
| conjunctival folliculosis | 2 (1.0%) | 9 (4.6%) | 1 (0.5%) |
| somnolence | 2 (1.0%) | 7 (3.6%) | 0 (0.0%) |

Adverse events led to the discontinuation of 3.6% (7/193) of patients in the Combination group, similar to 3.0% (6/197) of patients in the Timolol group, and statistically significantly less than 14.3% (28/196) of patients in the Brimonidine group (p<0.001). Serious adverse events were reported for 1.0% (2/193) of patients in the Combination group, 2.0% (4/196) of patients in the Brimonidine group, and 2.0% (4/197) of patients in the Timolol group. Two patients receiving Timolol had 4 serious adverse events (emphysema in one patient; nausea, sweating, and tachycardia in the other patient) which were considered possibly related to the study drug. There was 1 death in the Brimonidine group, possibly due to complications from cardiac surgery, and not related to study drug.

There were no clinically relevant differences between the Combination and either of the individual components in the mean change from baseline to month 3 for any hematology, chemistry, or urinalysis parameter. Statistically significant (p≦0.048) within-group changes from baseline were found, but were small and not clinically relevant.

Small but statistically significant (p≦0.001) mean reductions in heart rate ranging from −2.1 to −3.7 bpm were seen with the Combination, similar to Timolol. Small but statistically significant (p≦0.003) mean reductions in blood pressure at hour 2 (postdose) were seen with the Combination, similar to Brimonidine. These small changes in mean heart rate and blood pressure were associated with clinical symptoms in only a few patients.

Increases from baseline in the severity of conjunctival erythema and conjunctival follicles on biomicroscopy were statistically significantly less with the Combination than with Brimonidine (p≦0.011). The majority of patients in each treatment group showed less than a 2-line change from baseline visual acuity. There were no significant between-group differences for changes in visual fields or cup/disc ratio.

Pharmacokinetics:

Blood samples were available for 55 patients in the Combination group, 49 patients in the Brimonidine group, and 54 patients in the Timolol group. All samples were assayed for both brimonidine (lower limit of quantitation [LLOQ] 5 pg/mL) and timolol (LLOQ 5 pg/mL). Plasma brimonidine and timolol concentrations were not quantifiable in all but 1 sample on day 0, hour 0 for both Combination and the monotherapy treatment groups.

In the Combination group, mean±standard deviation (SD) plasma brimonidine concentrations 1 hour postdose at week 2 and month 3 were 49.7±36.1 and 52.8±46.7 pg/mL, respectively. In the Brimonidine group, mean±SD plasma brimonidine concentrations at week 2 and month 3 were 81.0±63.8 and 78.6±48.9 pg/mL, respectively. In the Combination group, mean±SD plasma timolol concentrations at week 2 and month 3 were 0.499±0.327 and 0.586±0.580 ng/mL, respectively. In the Timolol group, mean±SD plasma timolol concentrations at week 2 and month 3 were 0.950±0.709 and 0.873±0.516 ng/mL, respectively.

Plasma brimonidine and timolol concentrations 1 hour postdose were steady and did not increase over the 3-month study duration. Brimonidine concentrations were 39%, 34% and 39% lower in the Combination group than in the monotherapy group at week 2 (p=0.004), month 3 (p=0.013), and month 12, respectively. Timolol concentrations were 47% and 33% lower in the Combination group than in the monotherapy group at week 2 (p<0.001) and month 3 (p=0.011), respectively.

Timolol concentrations were also significantly lower in the combination treatment group than in the Timolol monotherapy treatment group (p=0.0006). Timolol concentrations were 49%, 32%, and 21% lower in the combination group than in the monotherapy group at week 2, month 3, and month 12, respectively.

The plasma brimonidine concentration in males was statistically significantly lower than in females for the Brimonidine group (37% lower at week 2 [p=0.034] and 37% lower at month 3 [p=0.017]); the difference was not statistically significant in the Combination group. The plasma timolol concentration in males was statistically significantly lower than in females for both the Combination group (not statistically significant at week 2; 52% lower at month 3 [p=0.012]) and the Timolol group (45% lower at week 2 [p=0.006] and 39% lower at month 3 [p=0.003]).

Plasma brimonidine concentration in the elderly group was not significantly different from in the young group for the combined data from both the combination and Brimonidine treatment groups (p-value=0.1323). However, plasma timolol concentration in the young group was significantly lower than in the elderly group for combined data from both the combination and the Timolol treatment groups (p-value=0.0005).

Conclusions

The Combination treatment (brimonidine tartrate 0.2%/timolol 0.5%) administered BID for 3 months was superior to Timolol (timolol 0.5%) BID and Brimonidine (brimonidine tartrate 0.2%) TID in lowering the elevated IOP of patients with glaucoma or ocular hypertension. The Combination administered BID demonstrated a favorable safety profile that was comparable to Timolol BID and better than Brimonidine TID with regard to the incidence of adverse events and discontinuations due to adverse events.

EXAMPLE II

A composition is prepared as described in Example I, except 0.5% timolol free base is used instead of timolol maleate. The composition is effective as described in Example I, but is more stable.

EXAMPLE II

A composition is prepared as described in Example I, except 0.5% timolol free base is used instead of timolol maleate. The composition is effective as described in Example I, but is more stable.

EXAMPLE III

A composition is prepared as described in Example I, except 0.5% timolol free base is used instead of timolol maleate and 0.18% brimonidine free base is used instead of brimonidine tartrate. The composition is effective as described in Example I, but is more stable.

The invention has been described herein by reference to certain preferred embodiments. However, as obvious variations thereon will become apparent to those skilled in the art, the invention is not to be considered as limited thereto.

The invention claimed is:

1. A composition comprising 0.2% brimonidine (w/v) and 0.5% timolol (w/v), in a single composition.

2. The composition of claim 1 further comprising from 0.001% to 0.01% benzalkonium chloride.

3. The composition of claim 2 comprising about 0.005% benzalkonium chloride.

4. The composition of claim 1 wherein brimonidine is brimonidine tartrate and timolol is timolol maleate.

5. The composition of claim 1 which is useful for treating ocular hypertension.

6. The composition of claim 1 which is useful for treating glaucoma.

7. An article of manufacture comprising packaging material and a composition within said packaging material, wherein said composition comprises 0.2% brimonidine by weight and 0.5% timolol by weight, in a single composition, and wherein said packaging indicates that the composition is useful for treating glaucoma or ocular hypertension by twice a day topical administration of the composition to a person's eye.

8. The article of manufacture of claim 7 wherein the composition further comprises from 0.001% to 0.01% benzalkonium chloride.

9. The article of manufacture of claim 7 wherein the composition further comprises about 0.005% benzalkonium chloride.

* * * * *